United States Patent
Cha et al.

(10) Patent No.: US 7,662,111 B2
(45) Date of Patent: Feb. 16, 2010

(54) VACUUM ASSISTED AUTO-LANCING DEVICE

(76) Inventors: Eun Jong Cha, Jukong Apt. 208-205, Mochung-Dong, Heungdeok-Gu, Cheongju-City, Chungcheongbuk-Do (KR); Mi Sook Park, 201-401, Hyundai 2 Apt. Yongam-Dong, Sangdang-Gu, Cheongju-City, Chungcheongbuk-Do (KR); Gang Cui, 19 Cho, Shinheungkamycongwhiwi, Younkil-So, Kilimsung (CN); Hak Hyun Nam, 102-206, Hanyang Apt, 133-1, Bun 3-Dong, Kangbuk-Gu, Seoul-City (KR); Geun Sig Cha, 9-78.Hongeun-Dong, Seodaemun-Gu, Seoul-City (KR)

( * ) Notice: Subject to any disclaimer, the term of this patent is extended or adjusted under 35 U.S.C. 154(b) by 750 days.

(21) Appl. No.: 10/530,195

(22) PCT Filed: Feb. 20, 2004

(86) PCT No.: PCT/KR2004/000351
§ 371 (c)(1),
(2), (4) Date: Nov. 18, 2005

(87) PCT Pub. No.: WO2005/030053
PCT Pub. Date: Apr. 7, 2005

(65) Prior Publication Data
US 2006/0155215 A1 Jul. 13, 2006

(30) Foreign Application Priority Data
Oct. 1, 2003 (KR) .................. 10-2003-0068213

(51) Int. Cl.
*A61B 5/00* (2006.01)

(52) U.S. Cl. .................................................. 600/583
(58) Field of Classification Search .................. 600/583, 600/584, 573, 576, 578, 579; 606/181–183
See application file for complete search history.

(56) References Cited

U.S. PATENT DOCUMENTS

| 4,637,403 A | 1/1987 | Garcia et al. |
| 5,423,847 A | 6/1995 | Strong et al. |
| 6,332,871 B1 | 12/2001 | Douglas et al. |

FOREIGN PATENT DOCUMENTS

| KR | 2000-0019996 U | * 11/2000 |
| KR | 10-2001-0025185 A | * 4/2001 |

* cited by examiner

*Primary Examiner*—Max Hindenburg
*Assistant Examiner*—Brian Szmal
(74) *Attorney, Agent, or Firm*—Birch, Stewart, Kolasch & Birch, LLP

(57) ABSTRACT

Disclosed herein is a vacuum assisted auto-lancing device. The device includes a housing (200) having a body (210) which has a lever hole. An actuating lever (300) includes an actuating switch (310) seated on the lever hole and having first and second actuating steps, a switch cap (320), and a switch cover (330). The device also includes a holding unit (400) having a first stem (410), a second stem (430), and a stem cap (450). A trigger (500) has a first trigger unit activated by the first actuating step, and a second trigger unit activated by the second actuating step. A lancet holder (524) holding a lancet (522) is secured to an end of the first trigger unit. The device includes a blood collecting unit (600) having an adjusting screw, an adjusting slider, and an end cap, and a vacuum unit (700) having a plunger and a body cap.

14 Claims, 10 Drawing Sheets

VACUUM ASSISTED AUTO-LANCING DEVICE

TECHNICAL FIELD

The present invention relates, in general, to vacuum assisted auto-lancing devices and, more particularly, to a vacuum assisted auto-lancing device, which is capable of drawing blood from a desired body site with a single operation regardless of the puncture site, and which is constructed so that there is no need to re-adjust the depth of penetration of a lancet into the skin whenever the lancing device is used, and which is constructed to easily create a vacuum, thus alleviating fear and pain experienced by a user, therefore affording comfort to the user.

BACKGROUND ART

Generally, a chronic diabetic must perform self blood glucose monitoring at home daily to maintain constant blood glucose. In order to do a blood glucose test, a sample of blood must be drawn from a body site. For example, a disposable lancet is driven to puncture skin at a selected body site, such as fingers, thus drawing a small amount of capillary blood. The sample of blood is applied to a strip. Next, the strip is placed in a test sensor to monitor blood glucose.

In order to draw blood from a body site, a lancing device has been widely used. The lancing device includes a lancet holder, an end cap, a spring, and a trigger. A disposable lancet is secured to the lancet holder. The end cap covers the lancet, and has a hole so that a tip of the lancet is propelled to the outside of the hole, thus puncturing the skin. Further, the spring and the trigger provide skin penetration force. The lancing device is used as follows. First, the end cap is removed from the lancing device, and the lancet is inserted in the lancet holder to compress the spring. In such a state, the end cap is closed. After assembly is completed, the lancing device comes into close contact with a body site having many capillary vessels, such as a finger. In such a state, a trigger switch is pressed to activate the lancet, thus puncturing the skin at the selected body site. At this time, an area around the puncture site is compressed, thus allowing a sufficient amount of capillary blood to be obtained. The sample of capillary blood is applied to a strip of a test sensor, and then blood glucose is measured. The method of drawing blood from the capillary vessels has been most widely used, but has a problem in that a patient must always carry the lancing device and a plurality of lancets.

In order to solve the problem, a disposable auto-lancet having a trigger is disclosed in Korean Patent Appln. No. 2000-55280. Such a disposable auto-lancet is advantageous in that there is no need to carry the lancing device. However, the disposable auto-lancet is problematic in that manufacturing costs thereof increases, thus imposing an economic burden on patients. Further, the conventional lancing device is problematic in that it is possible to draw blood only from a body site having many capillary vessels, for example, fingers or toes, so that a user experiences considerable pain due to nerve fibers which are distributed together with the capillary vessels, during the puncture of skin. Thereby, the conventional lancing device or the disposable auto-lancet causes anxiety to the user, such as a chronic diabetic who draws blood every day.

Recently, in order to solve the problems, a vacuum assisted lancing device is disclosed in U.S. Pat. No. 6,152,942. The vacuum assisted lancing device punctures skin at a body site having relatively few capillary vessels and nerve fibers, for example, an arm and a thigh, and then draws blood from the puncture site under vacuum pressure. The method of using the vacuum assisted lancing device is as follows. First, an end cap is removed from the lancing device, and a lancet is inserted in a lancet holder. Next, the end cap is closed again and then turned to a predetermined position on a ramp, thus adjusting a skin penetration depth. After the lancet has been mounted in the lancet holder, an end of the lancing device comes into close contact with the skin, and a plunger is pressed. At this time, the plunger is thrust into the lancing device to compress a spring which is placed in the lancing device. Simultaneously, a one-way check valve is opened, thus displacing air in the lancing device in proportional to the compression of the spring, therefore preventing internal pressure from increasing. By the movement of the plunger, the lancet moves to a predetermined position. At this time, drive and return springs and an actuator are operated, so that the lancet punctures the skin at a desired body site and then returns to an original position thereof.

As such, when the lancet punctures the skin and then the plunger is released, the spring pulls the plunger to create a vacuum in the end cap. At this time, the lancet is removed from the skin together with the plunger. When the plunger and the lancet are retracted from the skin, the skin bulges into the end cap due to the vacuum suction and blood is drawn from the skin. Thereafter, the plunger is pressed down to release the vacuum, and the lancing device is removed from the skin. Next, the blood is touched with a test sensor, thus monitoring blood glucose.

However, the conventional vacuum assisted lancing device has a problem in that the plunger must be pressed down to release the vacuum after blood has been drawn from a desired body site, so that the lancet coupled to the plunger may undesirably rebound and cause a second puncture. Such a second puncture may cause infection.

The conventional vacuum assisted lancing device has another problem in that the depth of penetration of the lancet into the skin is limited by the ramp of the end cap, so that special care is required to mount the end cap to a housing. Thus, whenever blood is drawn from a selected body site, the penetration depth must be re-adjusted.

Further, the conventional vacuum assisted lancing device obtains energy for compressing the spring and moves the lancet to a predetermined position, when the plunger is pressed down to create a vacuum. However, since the spring is strong, the plunger must be pressed with strong force to create a sufficient vacuum. Thus, this may cause anxiety about the skin puncture in a patient, thus provoking distaste for the use of the lancing device.

The conventional vacuum assisted lancing device has a further problem in that it is exclusively used for drawing blood from a desired body site under vacuum pressure, so that the lancing device cannot be used to draw blood from a body site having many capillary vessels, such as fingers or toes.

DISCLOSURE OF THE INVENTION

Accordingly, the present invention has been made keeping in mind the above problems occurring in the prior art, and an object of the present invention is to provide a vacuum assisted auto-lancing device, which is capable of drawing blood from a desired body site with a single operation regardless of the puncture site, and which is constructed so that there is no need to re-adjust the depth of penetration of a lancet into the skin whenever the lancing device is used, and which is constructed to automatically pierce the desired body site with weak force, thus alleviating the anxiety and pain experienced by a user, therefore affording comfort to the user.

BRIEF DESCRIPTION OF THE DRAWINGS

FIG. 3b is a sectional view to show a first partition plate provided in the body of FIG. 3a;

BEST MODE FOR CARRYING OUT THE INVENTION

In order to accomplish the above object, the present invention provides a vacuum assisted auto-lancing device, including a housing having a body, the body being partitioned into a first chamber and a second chamber by a first partition plate, with a lever hole provided on an outer periphery of the first chamber at a position adjacent to a first end of the first chamber, and a locking protrusion vertically protruding from a position around the lever hole; an actuating lever including an actuating switch seated on the lever hole and having at a lower portion thereof first and second actuating steps which pass through the lever hole, a switch cap covering the actuating switch, and a switch cover locking the actuating switch and the switch cap to a predetermined position of the body; a holding unit including a first stem coupled at a first end thereof to an inner periphery of the first chamber, a second end of the first stem being exposed to an outside of the first chamber, a second stem integrally coupled to the first end of the first stem and placed in the first chamber, and a stem cap to close a first end of the second stem; a trigger including a first trigger unit disposed at a position in the first and second stems and activated by the first actuating step, with a lancet holder holding a lancet and being secured to an end of the first trigger unit which extends to the first stem, and a second trigger unit rotatably mounted to cover both sides and a top of the second stem and activated by the second actuating step; a blood collecting unit including an adjusting screw positioned at the first end of the first chamber and rotatably secured to the first stem, an adjusting slider fastened to the adjusting screw, and an end cap mounted to the first stem; and a vacuum unit including a plunger placed to reciprocate in the second chamber and selectively passing through the first partition plate to engage with the second trigger unit, and a body cap to lock the plunger to the second chamber.

As described above, according to the present invention, it is possible to draw blood from a desired body site with a single operation regardless of puncture sites, and there is no need to re-adjust a penetration depth of a lancet into the skin whenever the lancing device is used, and a vacuum is created with weak force, thus alleviating fear and pain experienced by a user, therefore affording comfort to the user.

Hereinafter, the vacuum assisted auto-lancing device according to a preferred embodiment of the present invention will be described with reference to the accompanying drawings.

Figure 1:
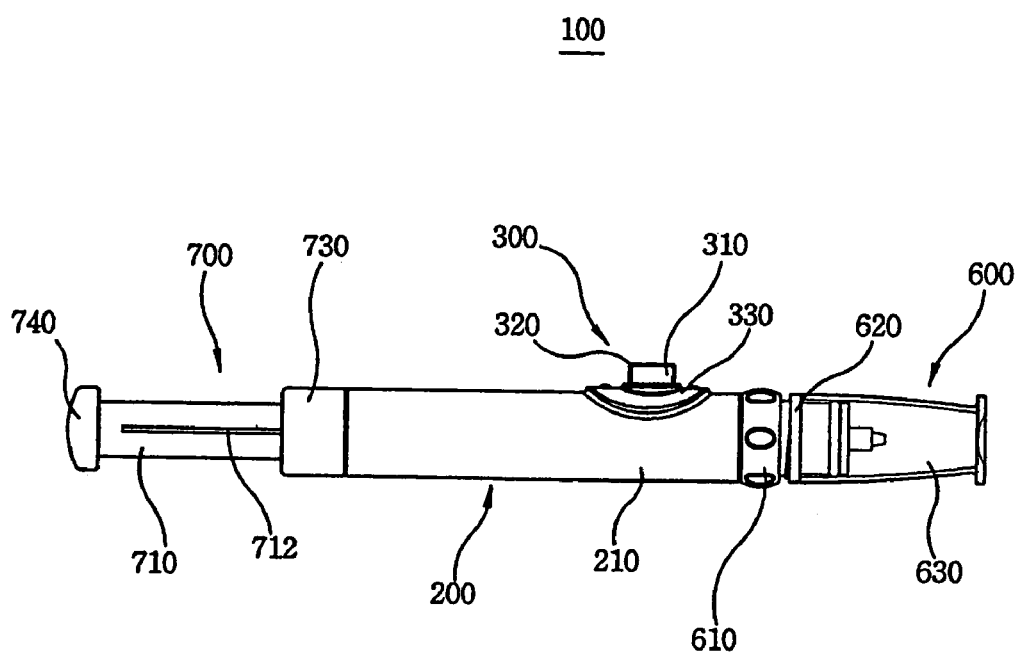
FIG. 1 is a front view to show a vacuum assisted auto-lancing device, according to the present invention.
Figure 2:
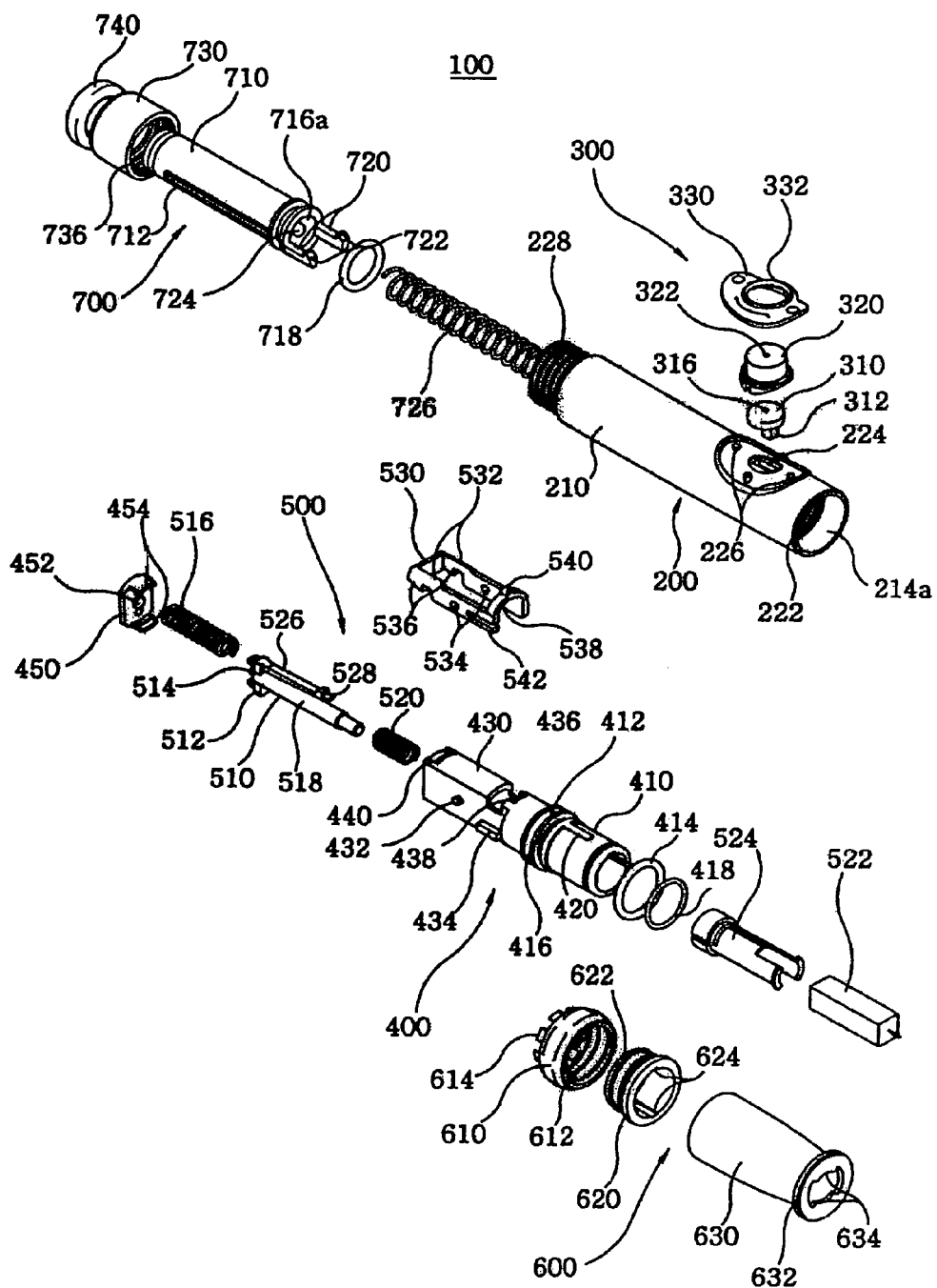
FIG. 2 is an exploded perspective view of the vacuum assisted auto-lancing device, according to the present invention.
Figure 3A:
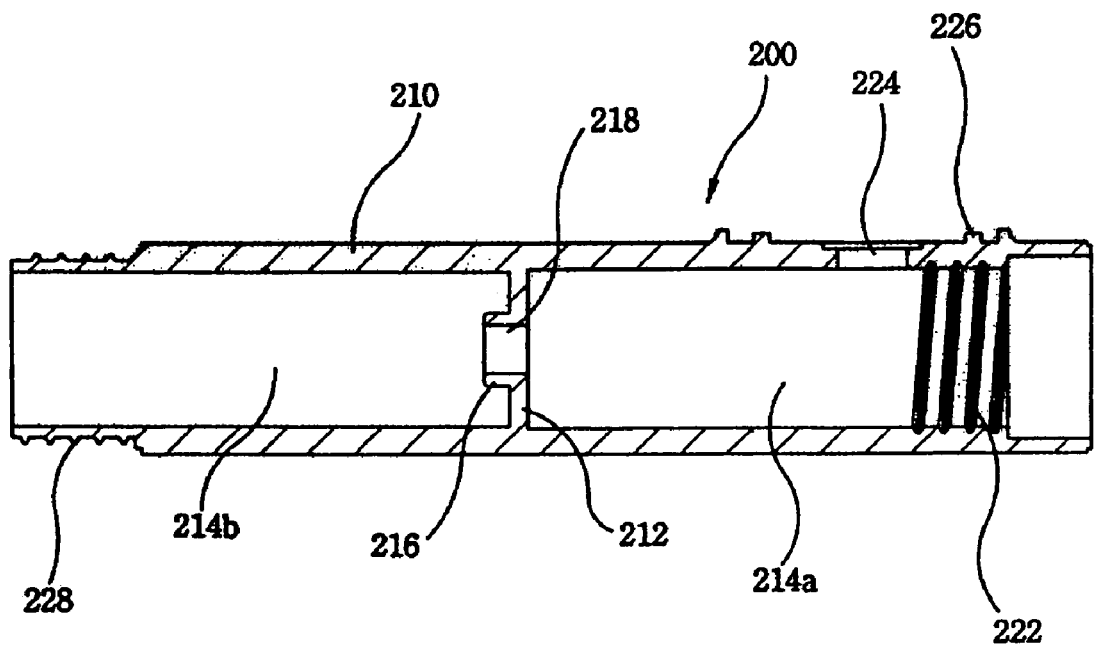
FIG. 3a is a sectional view to show an interior of a body included in the lancing device of FIG. 2.
Figure 3B:
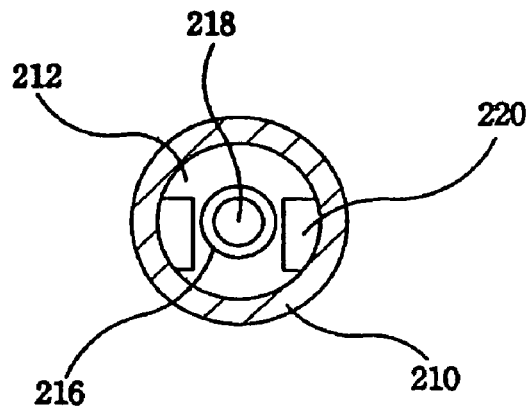
Figure 4A:
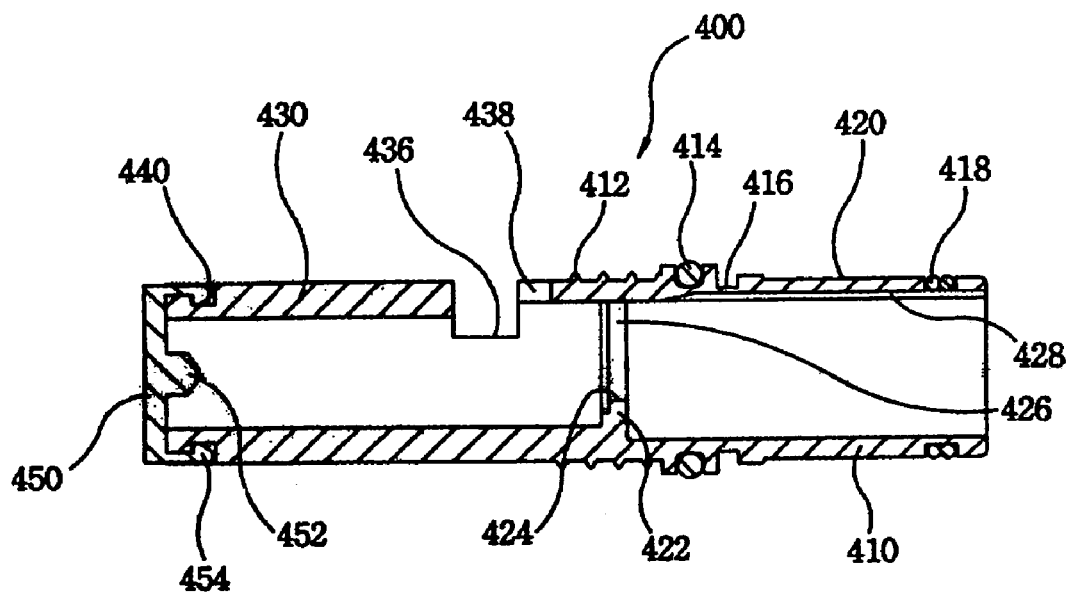
FIG. 4a is a sectional view to show an interior of a holding unit included in the lancing device of FIG. 2.
Figure 4B:
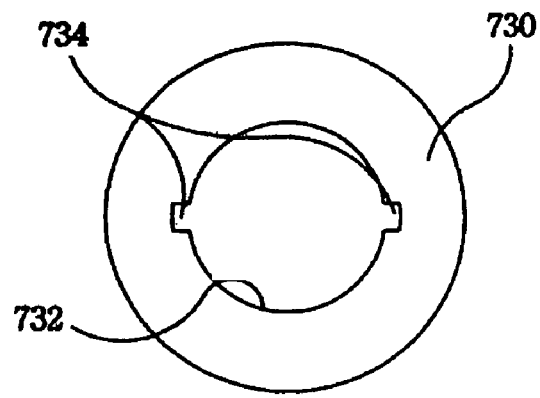
FIG. 4b is a view to show a surface of a body cap included in the lancing device of FIG. 2.

FIG. 1 is a front view to show a vacuum assisted auto-lancing device, according to the present invention, FIG. 2 is an exploded perspective view of the vacuum assisted auto-lancing device, according to the present invention, FIG. 3a is a sectional view to show an interior of a body included in the lancing device of FIG. 2, FIG. 3b is a sectional view to show a first partition plate provided in the body of FIG. 3a, FIG. 4a is a sectional view to show an interior of a holding unit included in the lancing device of FIG. 2, and FIG. 4b is a view to show a surface of a body cap included in the lancing device of FIG. 2.

Referring to FIGS. 1 and 2, the vacuum assisted auto-lancing device 100 according to the present invention includes a housing 200, an actuating lever 300 mounted to a predetermined position on the housing 200, a holding unit 400 installed at a predetermined position in the housing 200, a trigger 500 placed in the holding unit 400, a blood collecting unit 600, and a vacuum unit 700 mounted to an end of the housing 200.

The housing 200 has a body 210 which is open at opposite ends thereof. The body 210 is partitioned into a first chamber 214a and a second chamber 214b by a first partition plate 212 (see, FIG. 3a) that is provided in the body 210. A first spring mounting protrusion 216 (see, FIG. 3b) having an annular shape is provided on a central portion of the first partition plate 212 to protrude toward the second chamber 214b. A first guide hole 218 is provided at a predetermined position on the first spring mounting protrusion 216, and second guide holes 220 are provided on opposite sides of the first guide hole 218. A first internal threaded part 222 is provided on an inner periphery of the body 210 at a position adjacent to a first end of the first chamber 214a. Further, a lever hole 224 is bored in an upper portion of an outer periphery of the first chamber 214a, with a plurality of locking protrusions 226 being vertically formed around the lever hole 224. A first external threaded part 228 is provided on an outer periphery of a first end of the second chamber 214b.

The actuating lever 300 includes an actuating switch 310, a switch cap 320, and a switch cover 330. The actuating switch 310 having a disc shape is seated on the lever hole 224. A first actuating step 312 and a second actuating step 314 are provided on a lower surface of the actuating switch 310, and extend vertically to pass through the lever hole 224. In this case, the second actuating step 314 is shorter in length than the first actuating step 312 (see, FIG. 5a). A first vacuum hole 316 is formed on an upper surface of the actuating switch 310 to pass between the first and second actuating steps 312 and 314. The switch cap 320 is made of a flexible material to cover an outer surface of the actuating switch 310 and an outer surface of a portion of the body 210 while surrounding the actuating switch 310. A second vacuum hole 322 is formed on an upper portion of the switch cap 320 to communicate with the first vacuum hole 316. Further, the switch cover 330 has the same curvature as that of the outer periphery of the body 210, with a through hole 332 formed at a central portion of the switch cover 330 so that the actuating switch 310 surrounded by the switch cap 320 passes through the switch cover 330. A plurality of locking recesses 334 is provided on a lower surface of the switch cover 330, so that the locking protrusions 226 are fitted into the corresponding recesses 334 (see, FIG.

5a). That is, the holding unit 400, the trigger 500, and the blood collecting unit 600 are placed in the first chamber 214a of the body 210 to which the actuating lever 300 is secured, and the vacuum unit 700 coupled to the trigger 500 is placed in the second chamber 214b.

The holding unit 400 includes a first stem 410, a second stem 430, and a stem cap 450. The first stem 410 is placed in the first chamber 214a of the body 210. The second stem 430 is integrated with the first stem 410 to be placed in the first chamber 214a. The stem cap 450 closes a first end of the second stem 430. The first stem 410 has a cylindrical shape, and a second external threaded part 412 is provided on an outer periphery of a first end of the first stem 410 to correspond to the first internal threaded part 222. A first O-ring 414 is mounted to a portion around the second external threaded part 412 to be in close contact with the inner periphery of the first chamber 214a, thus sealing a gap between the first chamber 214a and the first stem. Further, an annular groove 416 is provided at a position around the first O-ring 414, and a second O-ring 418 is mounted to the outer periphery of a second end of the first stem 410. First guide rails 420 are provided on upper and lower portions of the outer periphery of the first stem 410 to extend from a position adjacent to the first O-ring 414 to the second O-ring 418. Further, a second partition plate 422 is integrally provided on the inner periphery of the first stem 410 adjacent to the first end of the first stem 410. A third guide hole 424 is formed at a central portion of the second partition plate 422, and a fourth guide hole 426 is provided above the third guide hole 424 and extends to the inner periphery of the first stem 410. Further, a first guide groove 428 is provided on an upper portion of the inner periphery of the first stem 410 and extends from a position adjacent to the fourth guide hole 426 to the second end of the first stem 410.

The second stem 430 has a box-like shape, which is formed such that upper and lower portions thereof are curved and both side surfaces thereof are vertically erected. Hinge shafts 432 protrude from central portions of the side surfaces of the second stem 430, and a stopper 434 is provided under either of the hinge shafts 432 and protrudes outwards. An upper portion of a second end of the second stem 430 is vertically cut out to provide a first depression 436, and a portion around the first depression 436 is horizontally cut out to provide a second depression 438. Locking holes 440 are provided on upper and lower portions of the first end of the second stem 430. The stem cap 450 has a plate shape which corresponds to a shape of the second end of the second stem 430. A second spring mounting protrusion 452 protrudes from a central portion on a surface of the stem cap 450, and locking steps 454 are provided on upper and lower portions of the stem cap 450 to be fitted into the locking holes 440. The trigger 500 and the blood collecting unit 600 are placed in the holding unit 400.

The trigger 500 is provided with a first trigger unit 510 placed at a position in the first and second stems 410 and 430, a lancet holder 524 mounted to the first trigger unit 510, and a second trigger unit 530 rotatably placed at an upper portion of the second stem 430. The first trigger unit 510 includes a vertical base plate 512, a joint bar 518, and a lancet locking plate 526. The base plate 512 is vertically placed in the second stem 430. A third spring mounting protrusion 514 is integrally provided on a first surface of the base plate 512 to correspond to the second spring mounting protrusion 452. A lancet spring 516 is placed between the second and third spring mounting protrusions 452 and 514. Further, the joint bar 518 and the lancet locking plate 526 are provided on a second surface of the base plate 512. The joint bar 518 extends horizontally from a central portion of the base plate 512 through the third guide hole 424 to the first stem 410. A rebound spring 520 is fitted over the joint bar 518, and the lancet holder 524 holding a lancet 522 is mounted to an end of the joint bar 518 which passes through the third guide hole 424. The lancet locking plate 526 is provided on an upper portion of the second surface of the base plate 512, and passes through the fourth guide hole 426 to be disposed in the first guide groove 428, in a manner similar to the joint bar 518. A first trigger protrusion 528 is provided at an upper portion of an end of the lancet locking plate 526. When the lancet 522 is inserted in the lancet holder 524, the first trigger protrusion 528 becomes seated in the second depression 438 and is struck by the first actuating step 312. The second trigger unit 530 has seesaw plates 432 contacting both side surfaces of the second stem 430, and a plunger locking plate 538 coupling the seesaw plates 532 to each other. The seesaw plates 432 have hinge holes 534 to rotatably receive the hinge shafts 432 that are provided on both side surfaces of the second stem 430. A first hook 536 is provided at a lower portion of a first side of each of the hinge holes 534. An elastic piece 542 is integrally provided at a lower portion of a second side of either of the seesaw plates 532 such that a lower surface of the elastic piece 542 is in close contact with an upper surface of the stopper 434. Further, the plunger locking plate 538 having a dome shape is placed on upper ends of the seesaw plates 532. The plunger locking plate 538, which couples the seesaw plates 532 to each other, is seated on the first depression 436, and the lancet locking plate 526 is located under the locking plate 538. A second trigger protrusion 540 is provided on an upper surface of the plunger locking plate 538 to protrude upwards, and is selectively struck by the second actuating step 314.

The blood collecting unit 600 is disposed at the first end of the first chamber 214a, and includes an annular adjusting screw 610 rotatably secured to the first stem 410, an adjusting slider 620 fastened to the adjusting screw 610, and an end cap 630. The adjusting screw 610 has the shape of an annular ring which has on an inner periphery thereof a depth adjusting internal threaded part 612. Further, a plurality of rotary protrusions 614 having a hook shape is provided on an end of the adjusting screw 610 to protrude radially, and engages with the annular groove 416 of the first stem 410. The adjusting slider 620 has the shape of an annular ring, like the adjusting screw 610. A depth adjusting external threaded part 622 is provided on an outer periphery of the adjusting slider 620 to correspond to the depth adjusting internal threaded part 612. Second guide grooves 624 are provided on upper and lower portions of an inner periphery of the adjusting slider 620 to engage with the first guide rails 420 of the first stem 410. That is, the adjusting slider 620 moves forwards and backwards due to the engagement of the first guide rails 420 with the second guide grooves 624. The end cap 630 has the shape of a cylinder which is opened at opposite ends thereof and is tapered in a predetermined direction. Stabilizing protrusions 634 are integrally provided on both sides of an inner periphery of an end of the end cap 630 and extend inwards. Preferably, the stabilizing protrusions 634 form a hole in a butterfly shape in cooperation with an end of the end cap 630, thus allowing the lancet 522 to be re-arranged by simply turning the end cap 630 upside down. Further, a contact plate 632 is integrally provided on the end of the end cap 630 and comes into close contact with user's skin. The end cap 630 is made of a transparent material to allow the user to observe collected blood. The end cap 630 is fitted over the holding unit 400 so that an inner periphery of the end cap 630 is in close contact with an outer periphery of the second O-ring 418. Further, the contact plate 632 has the shape of a flange which radially extends outwards from the end of the end cap 630. The contact plate 632 is upwardly curved to be in close contact with a puncture site. As such, the holding unit 400, the trigger 500, and the blood collecting unit 600 are positioned in the housing 200, with the vacuum unit 700 arranged in the second chamber 214b of the housing 200.

The vacuum unit 700 is provided with a plunger 710, a body cap 730, and a plunger cap 740. The plunger 710 has a cylindrical shape to reciprocate in the second chamber 214b, and second guide rails 712 are provided on both sides of an outer periphery of the plunger 710. The plunger 710 is partitioned into a third chamber 716a and a fourth chamber 716b by a third partition plate 714, like the body 210. A third O-ring 718 is fitted over an end of the third chamber 716a and is in close contact with the inner periphery of the second chamber 214b. Mounting plates 720 are provided on both sides of the end of the third chamber 716a and extend horizontally, and are selectively fitted into the second guide holes 220. A second hook 722 is provided on an upper end of each mounting plate 720 to engage with the first hook 536. A fourth spring mounting protrusion 724 is provided in the third chamber 716a, extends from the third partition plate 714, and faces the first spring mounting protrusion 216. A plunger spring 726 is positioned between the first and second spring mounting protrusions 216 and 724. The body cap 730 has the shape of a cylinder which is opened at a first end and closed at a second end thereof. An annular plunger hole 732 is formed on the second end of the body cap 730 to allow the plunger 710 to move in and out of the body cap 730. Further, third guide grooves 734 are provided on opposite sides of the plunger hole 732 to guide the second guide rails 712. A second internal threaded part 736 is provided on an inner periphery of the body cap 730 to correspond to the first external threaded part 228. The plunger cap 740 is detachably mounted to the fourth chamber 716b of the plunger 710 which is exposed to the outside of the body cap 730. Such a plunger cap 740 is made of a flexible material. Further, a strip 742 for testing blood glucose is provided in the fourth chamber 716b which is closed by the plunger cap 740.

The assembly of the vacuum assisted auto-lancing device 100 constructed as described above will be described below in brief.

When a user wishes to operate the vacuum assisted auto-lancing device 100, first, the trigger 500 is mounted to the holding unit 400. After the rebound spring 520 is mounted to the joint bar 518 of the first trigger unit 510, the first trigger unit 510 is installed so that an end of the joint bar 518 passes through the third guide hole 424. Further, the first trigger protrusion 528 of the lancet locking plate 526 is inserted into the first guide groove 428. Next, the lancet holder 524 is secured to the joint bar 518 which is exposed to the outside of the third guide hole 424. Afterwards, the lancet spring 516 is arranged such that an end thereof is supported by the third spring mounting protrusion 514 of the base plate 512 and the other end thereof is supported by the second spring mounting protrusion 452 of the stem cap 450. In such a state, the locking steps 454 of the stem cap 450 are fitted into the locking holes 440 of the second stem 430, thus closing the second stem 430. After the first trigger unit 510 is thus mounted, the second trigger unit 530 is mounted to the holding unit 400. In order to mount the second trigger unit 530, the seesaw plates 532 are rotatably mounted to the second stem 430. That is, the hinge shafts 432 of the second stem 430 are inserted into the hinge holes 534 of the seesaw plates 532. The elastic piece 542 provided on either of the seesaw plates 532 is seated on the stopper 450. The plunger locking plate 538 is disposed to surround the upper portion of the first depression 436.

After the trigger 500 has been mounted to the holding unit 400, the first and second O-rings 414 and 418 are fitted over the first stem 410. In such a state, the holding unit 400 is installed in the body 210 of the housing 200. At this time, the second external threaded part 412 of the first stem 410 is fastened to the first internal threaded part 222 provided on the first chamber 214a of the body 210. As such, when the holding unit 400 is installed in the first chamber 214a, the first trigger protrusion 528 and the second trigger protrusion 530 are disposed at positions around the lever hole 224. After the holding unit 400 equipped with the trigger 500 is installed in the body 210, the vacuum unit 700 and the actuating lever 300 are installed. First, the adjusting screw 610 of the blood collecting unit 600 is fitted over the first chamber 214a which is exposed to the outside, and then pressed so that the rotary protrusions 614 of the adjusting screw 610 engage with the annular groove 416. In such a state, the adjusting slider 620 is fastened to the adjusting screw 610. Next, after the second guide grooves 624 of the adjusting slider 620 are placed near the first guide rails 420 of the first stem 410, the adjusting screw 610 is rotated in a predetermined direction. At this time, the adjusting slider 620 moves along the first guide rails 420 and is fastened to the adjusting screw 610. Thereafter, the end cap 630 is secured to a portion of the first stem 410 which is exposed to the outside of the adjusting slider 620. At this time, the inner periphery of the end cap 630 is in close contact with the outer periphery of the second O-ring 418 fitted over the first stem 410.

After the assembly of the blood collecting unit 600 has been completed, the actuating lever 300 is mounted to the body 210. First, the actuating switch 310 is aligned above the lever hole 224, and then the first and second actuating steps 312 and 314 are fitted into the lever hole 224. At this time, a lower portion of the first actuating step 312 is spaced apart from the first trigger protrusion 528 of the lancet locking plate 526, and a lower portion of the second actuating step 314 is adjacent to the second trigger protrusion 540. After the actuating switch 310 is arranged, the upper portion of the actuating switch 310 is covered by the switch cap 320, and the switch cover 230 is secured to the body 210 to limit movement of the actuating switch 310 and the switch cap 320. At this time, the actuating switch 310 covered by the switch cap 320 is exposed to the outside through the through hole 332 of the switch cover 230. The locking recesses 334 provided on the switch cover 230 engage with the locking protrusions 226.

In order to mount the vacuum unit 700 to the second chamber 214b of the body 210, the third O-ring 718 is fitted over the plunger 710. Next, the plunger 710 is inserted in the second chamber 214b while an end of the plunger spring 726 is disposed in the third chamber 716a. After the plunger 710 is inserted in the second chamber 214b, the body cap 740 covers a portion of the plunger 710 which is exposed to the outside of the second chamber 214b. In such a state, the body cap 740 is turned so that the second internal threaded part 736 of the body cap 740 engages with the first external threaded part 228 of the second chamber 228. At this time, the mounting plates 720 provided on the plunger 710 are disposed to move in and out of the second guide holes 220, and the other end of the plunger spring 726 is supported by the first spring mounting protrusion 216. The second guide rails 712 of the plunger 710 engage with the third guide grooves 734 of the body cap 740, thus preventing idle rotation of the plunger 710. When the plunger 710 has been mounted, the testing strip 742 is put into the fourth chamber 716b of the plunger 710, and the fourth chamber 716b is closed by the plunger cap 740.

The operation of the vacuum assisted auto-lancing device 100 constructed as described above will be described below in brief.

Figure 5A:
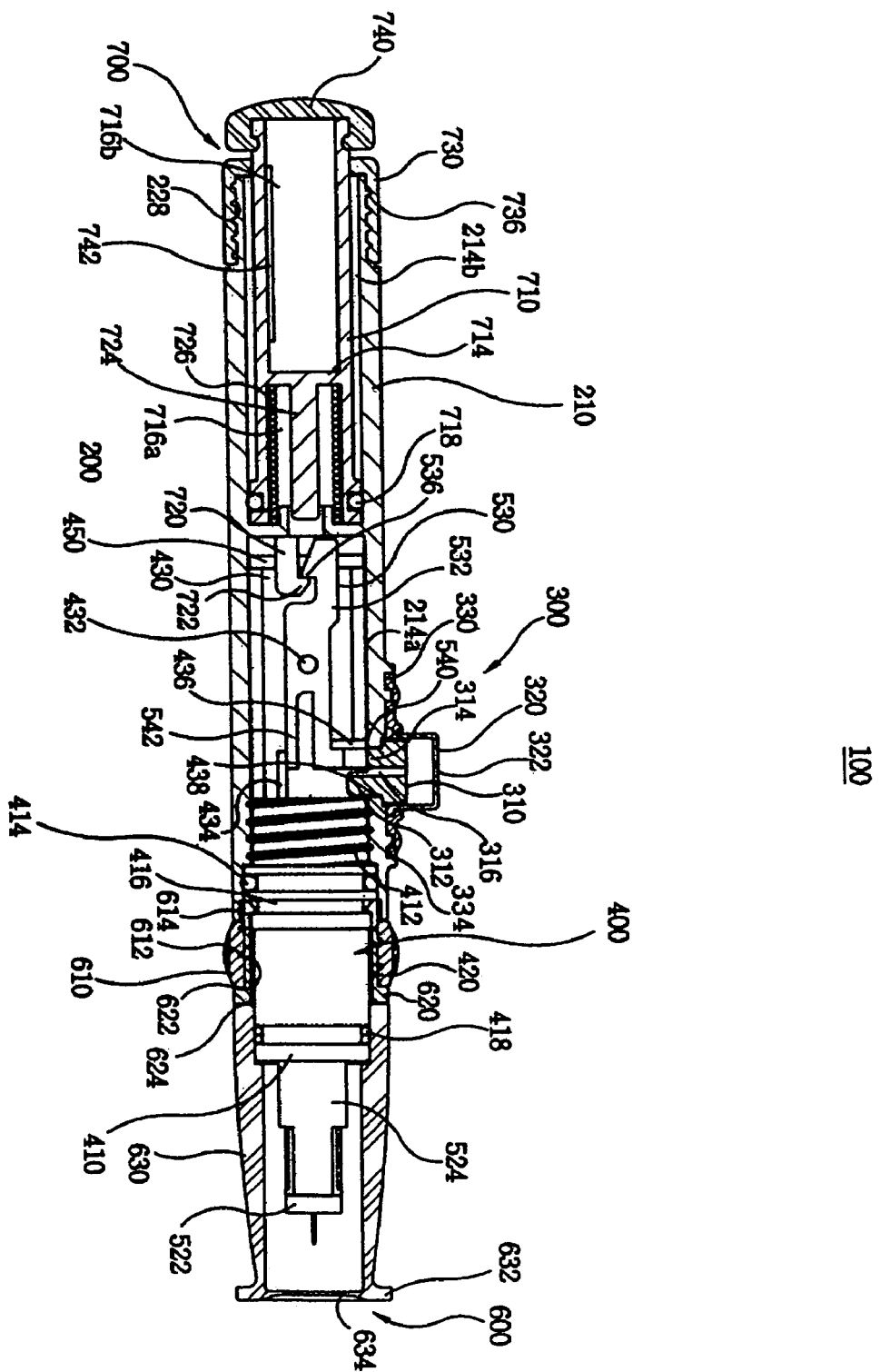
FIGS. 5a and 5b are sectional views to show the triggering waiting state of the vacuum assisted auto-lancing device, according to the present invention.
Figure 5B:
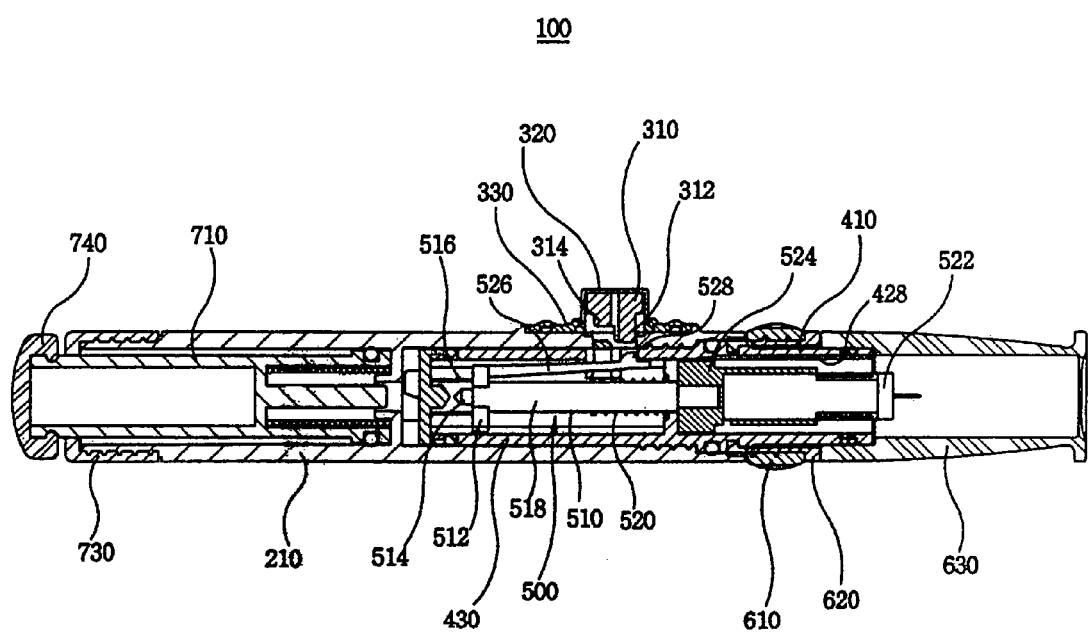
Figure 6A:
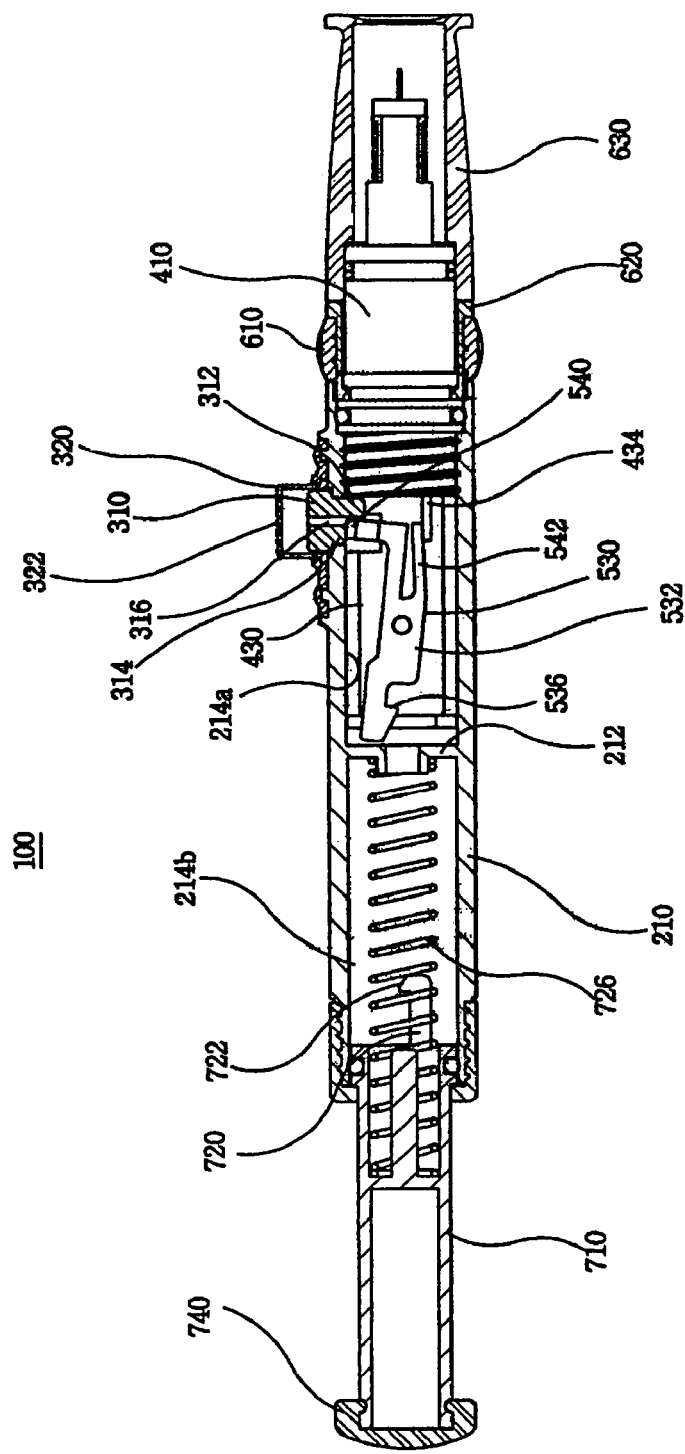
FIGS. 6a and 6b are sectional views to show the state where a plunger and a lancet included in the lancing device of FIGS. 5a and 5b are triggered.
Figure 6B:
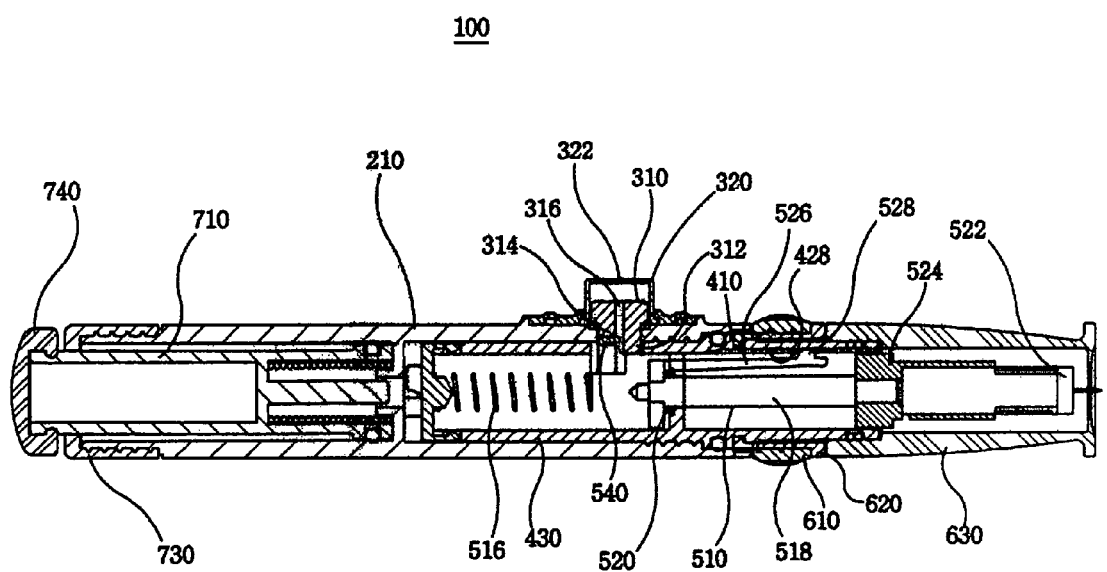
Figure 7A:
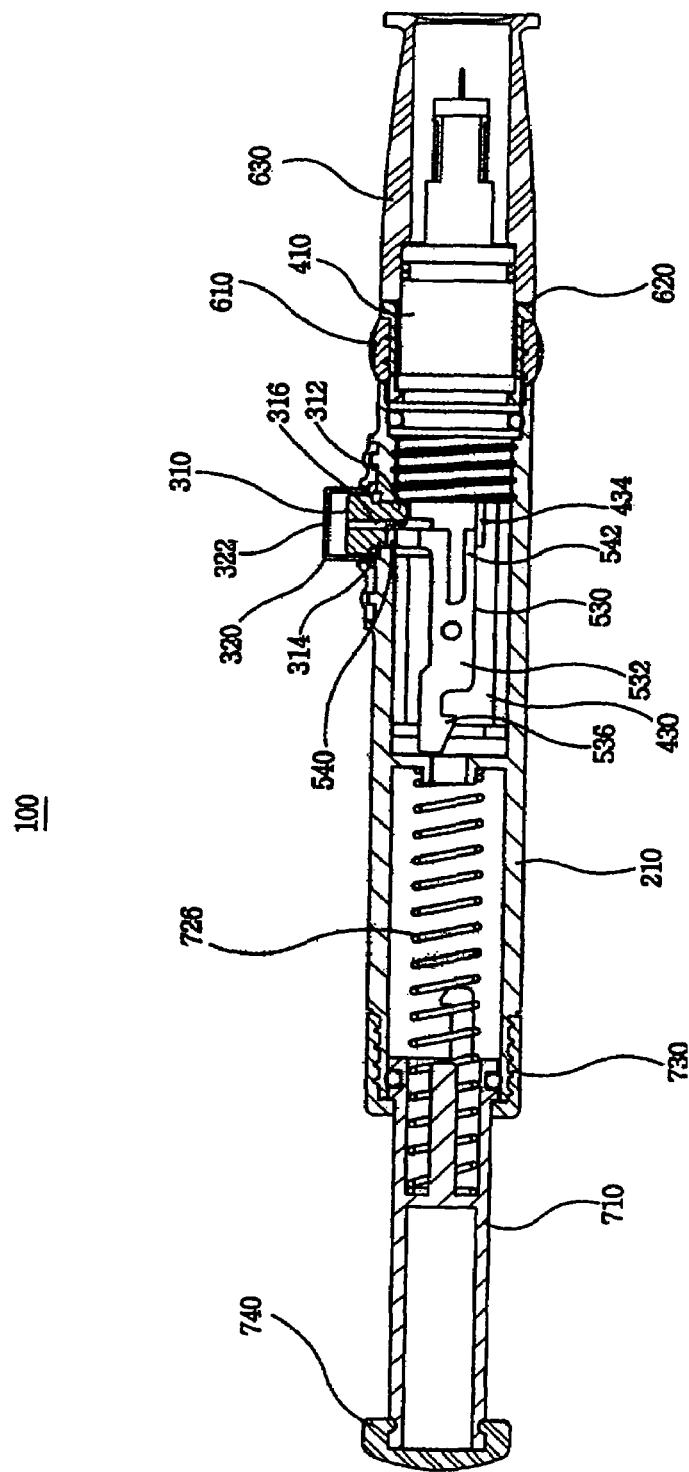
FIGS. 7a and 7b are sectional views to show the state where the plunger and the lancet of FIGS. 5a and 5b are released.
Figure 7B:
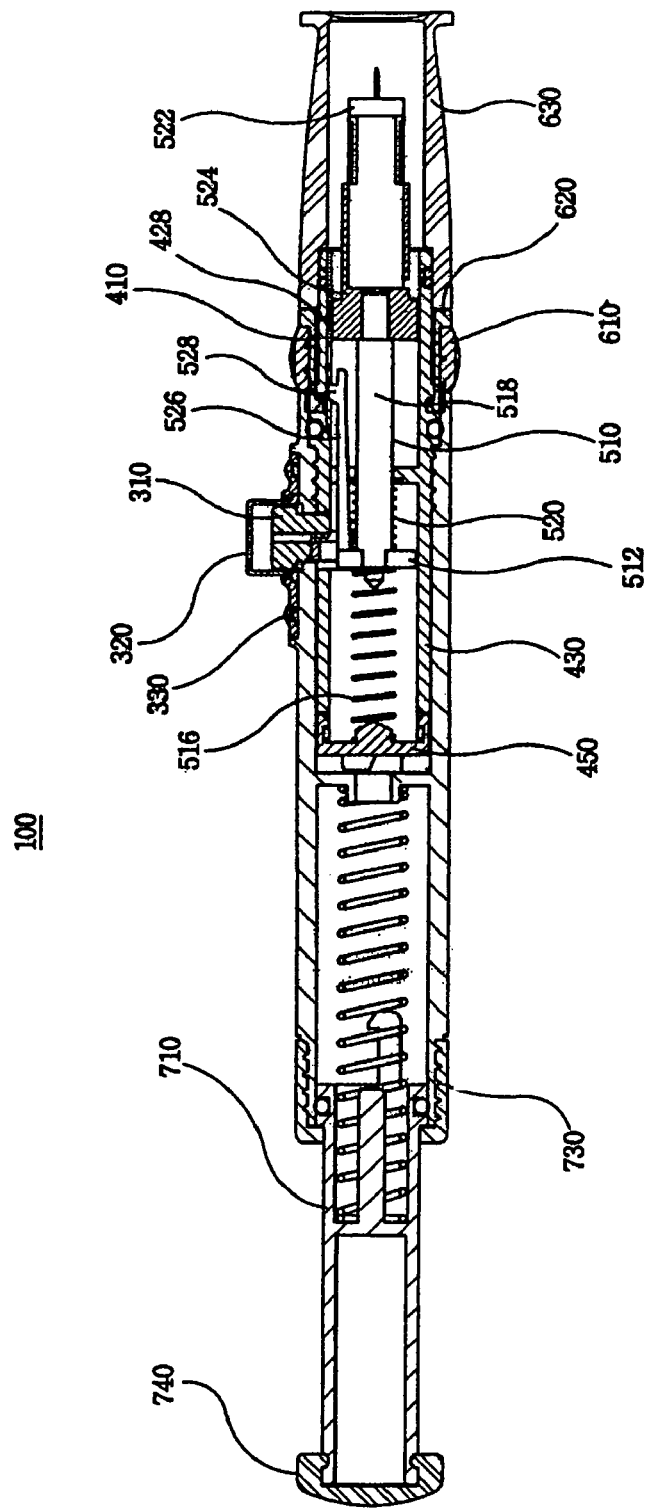

FIGS. 5a and 5b are sectional views to show the triggering waiting state of the vacuum assisted auto-lancing device, according to the present invention, FIGS. 6a and 6b are sectional views to show the state where a plunger and a lancet included in the lancing device of FIGS. 5a and 5b are triggered, and FIGS. 7a and 7b are sectional views to show the state where the plunger and the lancet of FIGS. 5a and 5b are released.

Referring to FIGS. 5a to 7b, when a user desires to use the vacuum assisted auto-lancing device 100 according to the present invention, the end cap 630 is removed from the device, and the lancet 522 is mounted to the lancet holder 524. While the lancet 522 is mounted to the lancet holder 524, the lancet holder 524 presses the lancet spring 516 so that the first trigger protrusion 528 of the first trigger unit 510 engages with the second depression 438 (see, FIG. 5b). Preferably, the distance between the first actuating step 312 and the first trigger protrusion 528 is shorter than the distance between the second actuating step 314 and the second trigger protrusion 540. Thus, after the first trigger protrusion 528 is struck by the first actuating step 312, the second trigger protrusion 540 is struck by the second actuating step 314. Thereby, the triggering operation can be automatically performed in stages. Next, the adjusting screw 610 is turned to determine the depth of penetration of the lancet 522 by the adjusting slider 620. Afterwards, the end cap 630 is closed again.

When the above-mentioned operation has been completed, the user grasps the body 210 and presses the plunger cap 740 (see, FIG. 5a). At this time, the pressed plunger 710 compresses the plunger spring 726, and thereby the mounting plates 720 move into the second guide holes 220. At this time, the second hooks 722 provided on the mounting plates 720 engage with the first hooks 536 provided on the seesaw plates 532 of the second trigger unit 530. When the plunger 710 is thus pressed, the contact plate 632 of the end cap 630 comes into contact with skin at a puncture site. In such a state, the actuating switch 310 is pressed while closing both the second vacuum hole 322 and the first vacuum hole 316. At this time, air in the lancing device 100 is compressed and the first trigger unit 510 is activated (see, FIG. 6b). That is, the first actuating step 312 moves downwards to strike the first trigger protrusion 528. The struck first trigger protrusion 528 is removed from the second depression 438 and is activated by elastic force of the compressed lancet spring 516. Thereby, the lancing device punctures the skin. Subsequently, the first trigger protrusion 528 is returned to an original position thereof by the rebound spring 520. The first trigger protrusion 528, which has been removed from the second depression 438, is held in the first guide groove 428 of the first stem 410. In this case, the plunger 710 is triggered, as soon as the first trigger unit 510 is operated (see, FIG. 6a). After the first actuating step 312 strikes the first trigger protrusion 528, the second actuating step 314 strikes the second trigger protrusion 540 of the second trigger unit 530. The struck second trigger protrusion 540 lifts the seesaw plates 532 upwards. At this time, the first hooks 536 of the seesaw plates 532 disengage from the second hooks 722. The elastic piece 542 is compressed against the stopper 434, and simultaneously the plunger 710 is moved backwards in the second chamber 214b by the plunger spring 726. At this time, the second trigger unit 530 returns to an original position thereof by the elastic piece 542 which is compressed against the stopper 434. As such, when the plunger 710 and the first trigger unit 510 are released (see, FIGS. 7a and 7b), the pressure in the lancing device 100 decreases, so that blood is drawn from a puncture site which is formed by the lancet 522. When a predetermined amount of blood has been collected, the actuating switch 310 is operated to open both the second vacuum hole 322 and the first vacuum hole 316. Air is fed into the lancing device 100 to release the vacuum. Next, the lancing device 100 is removed from the skin. Thereafter, the strip 742 is taken out of the fourth chamber 716b and blood glucose is monitored.

INDUSTRIAL APPLICABILITY

As described above, the present invention provides a vacuum assisted auto-lancing device 100, which is constructed so that a lancet 522 mounted to a first trigger unit 510 and a plunger 710 are separately operated, thus preventing double puncture, and which can use only one of the lancet 522 and the plunger 710, thus being very convenient to reuse, even when a user makes a mistake during the use of the lancing device, and which may be applied to all body sites, including fingers and arms, and which is automatically triggered by a simple manipulation of the actuating switch 310, thus alleviating anxiety about the use of the lancet, and affording constant and instant skin penetration.

Further, an end cap 630 is assembled after a skin penetration depth is adjusted beforehand by an adjusting screw 610, so that it is unnecessary to adjust the skin penetration depth every time, unlike the conventional vacuum assisted lancing device, and damage to hypodermic tissue is prevented.

Furthermore, a contact plate 632 of the end cap 630 is curved upwards, thus allowing the contact area between the contact plate and the skin to be increased when the skin bulges due to vacuum suction, and allowing blood to be uniformly drawn from capillary vessels, therefore efficiently drawing blood from a body site. By closing or opening a first vacuum hole 316 and a second vacuum hole 322, a vacuum is easily created or released, thus preventing the spillage of blood which may occur when a conventional lancing device is removed from a body site under vacuum pressure.

The invention claimed is:

1. A vacuum assisted auto-lancing device, comprising:
a housing having a body, the body being partitioned into a first chamber and a second chamber by a first partition plate, with a lever hole provided on an outer periphery of the first chamber at a position adjacent to a first end of the first chamber, and a locking protrusion vertically protruding from a position around the lever hole;
an actuating lever, comprising:
an actuating switch seated on the lever hole, and having at a lower portion thereof first and second actuating steps which pass through the lever hole;
a switch cap covering the actuating switch; and
a switch cover locking the actuating switch and the switch cap to a predetermined position of the body;
a holding unit, comprising:
a first stem coupled at a first end thereof to an inner periphery of the first chamber, a second end of the first stein being exposed to an outside of the first chamber;
a second stem integrally coupled to the first end of the first stem and placed in the first chamber; and
a stem cap to close a first end of the second stem;
a trigger comprising:
a first trigger unit disposed at a position in the first and second stems, and activated by a first actuating step, with a lancet holder holding a lancet and being secured to an end of the first trigger unit which extends to the first stem; and a second trigger unit rotatably mounted to cover both sides and a top of the second stem, and activated by a second actuating step;

a blood collecting unit, comprising:
an adjusting screw positioned at the first end of the first chamber and rotatably secured to the first stem;
an adjusting slider fastened to the adjusting screw; and
an end cap mounted to the first stem; and a vacuum unit, comprising:
a plunger placed to reciprocate in the second chamber, and selectively passing through the first partition plate to engage with the second trigger unit; and
a body cap to lock the plunger to the second chamber.

2. The vacuum assisted auto-lancing device according to claim 1, wherein the actuating switch is configured so that the second actuating step thereof is shorter in length than the first actuating step thereof, and a first vacuum hole extends from an upper portion of the actuating switch and passes between the first and second actuating steps, and the switch cap is made of a flexible material to seal a gap between the actuating switch and the outer periphery of the body, with a second vacuum hole formed on an upper surface of the switch cap to communicate with the first vacuum hole, and the switch cover has at a central portion thereof a through hole to allow the actuating switch surrounded by the switch cap to pass through the switch cover, with a plurality of locking recesses provided on a lower surface of the switch cover to engage with the locking protrusions.

3. The vacuum assisted auto-lancing device according to claim 1, wherein the first partition plate has on a central portion thereof a first spring mounting protrusion protruding toward the second chamber, with a first guide hole formed at a predetermined position on the first spring mounting protrusion, and second guide holes formed on opposite sides of the first guide hole, and a first external threaded part is provided on an outer periphery of a first end of the second chamber, and a first internal threaded part is provided on the inner periphery of the first chamber at a position adjacent to the first end of the first chamber.

4. The vacuum assisted auto-lancing device according to claim 3, wherein the holding unit further comprises: a second external threaded part provided on an outer periphery of the first end of the first stem of the holding unit to correspond to the first internal threaded part; a first o-ring mounted to a position around the second external threaded part to seal a gap between the inner periphery of the first chamber and an outer periphery of the first stem; an annular groove provided at a position around the first o-ring; a second o-ring fitted over the second end of the first stem that is exposed to an outside of the first chamber; and a second partition plate integrally mounted to an inner periphery of the first end of the first stem, with a third guide hole formed at a central portion of the second partition plate, and a fourth guide hole provided above the third guide hole to extend to the inner periphery of the first stem.

5. The vacuum assisted auto-lancing device according to claim 4, wherein first guide rails are provided on upper and lower portions of the outer periphery of the first stem to extend from the first o-ring to the second o-ring, and a first guide groove is provided on an upper portion of the inner periphery of the first stem to extend from a position around the fourth guide hole to the second end of the first stem.

6. The vacuum assisted auto-lancing device according to claim 5, wherein the second stem comprises: hinge shafts protruding from both side surfaces of the second stem, with a stopper protruding from a position under either of the hinge shafts; a first depression provided by vertically cutting out an upper portion of the second end of the second stem; a second depression provided by horizontally cutting out a portion around the first depression; and locking holes provided on upper and lower portions of the first end of the second stem, a stem cap being mounted to the first end of the second stem and having the same shape as the first end of the second stem, with a second spring mounting protrusion provided on a surface of the stem cap and locking steps provided on upper and lower portions of the stem cap to be fitted into the corresponding locking holes.

7. The vacuum assisted auto-lancing device according to claim 6, wherein the first trigger unit of the trigger comprises: a base plate vertically placed in the second stem, with a third spring mounting protrusion provided at a central portion on a first surface of the base plate to face the second spring mounting protrusion and support a lancet spring; a joint bar extending from a second surface of the base plate to a predetermined position to pass through the third guide hole, with a rebound spring fitted over the joint bar, and the lancet holder holding the lancet secured to an end of the joint bar which passes through the third guide hole; and a lancet locking plate provided at an upper position on the second surface of the base plate to pass through the fourth guide hole and extend to the first guide groove, with a first trigger protrusion provided at an upper position of an end of the lancet locking plate and selectively engaging with the second depression to be struck by the first actuating step.

8. The vacuum assisted auto-lancing device according to claim 6, wherein the second trigger unit comprises: seesaw plates each having at a central portion thereof a hinge hole to rotatably engage with the corresponding hinge shaft, with a first hook provided at a lower portion on a first side of the hinge hole of each of the seesaw plates, and an elastic piece provided at a lower portion on a second side of either of the seesaw plates to be in close contact with an upper surface of the stopper; a plunger locking plate coupling upper edges of the seesaw plates to each other, and seated in the first depression; and a second trigger protrusion provided at an upper portion of the plunger locking plate to be struck by the second actuating step.

9. The vacuum assisted auto-lancing device according to claim 6, wherein the adjusting screw of the blood collecting unit has a shape of an annular ring, with a depth adjusting internal threaded part provided on an inner periphery of the adjusting screw, and a plurality of rotary protrusions having hook shapes protruding radially to be rotatably fitted into the annular groove, and the adjusting slider has a shape of an annular ring, with a depth adjusting external threaded part provided on an outer periphery of the adjusting slider to correspond to the depth adjusting internal threaded part, and second guide grooves formed on upper and lower portions of an inner periphery of the adjusting slider to engage with the first guide rails, and the end cap has a shape of a cylinder which is opened at both ends thereof and tapered in a predetermined direction, with an upper portion of an inner periphery of the end cap coming into close contact with the second o-ring of the first stem.

10. The vacuum assisted auto-lancing device according to claim 9, wherein the end cap further comprises stabilizing protrusions which integrally extend inwards from both sides of a lower portion on the inner periphery of the end cap.

11. The vacuum assisted auto-lancing device according to claim 9, wherein the end cap is made of a transparent material to allow a user to observe collected blood, and a contact plate having a flange shape is integrally provided at an end of the end cap and radially extends outwards from the end of the end cap, the contact plate being curved upwards to be in close contact with a predetermined body site.

12. The vacuum assisted auto-lancing device according to claim 9, wherein the plunger of the vacuum unit has second guide rails on both sides of an outer periphery of the plunger, and an interior of the plunger is partitioned into a third chamber and a fourth chamber by a third partition plate, and a third o-ring is fitted over an end of the third chamber and is in close contact with the inner periphery of the second chamber, and mounting plates are provided on both sides of the end of the third chamber and horizontally extend to an outside of the third chamber, thus selectively passing through the second guide holes, with a second hook provided on an upper end of each of the mounting plates to engage with the first hook, and a fourth spring mounting protrusion is provided in the third chamber and extends from the third partition plate to face the first spring mounting protrusion and support the plunger spring.

13. The vacuum assisted auto-lancing device according to claim 12, wherein the body cap is shaped so that a first end thereof is opened and a second end thereof is closed, the body cap comprising a plunger hole provided on the second end of the body cap to allow the plunger to move in and out of the body cap, third guide grooves provided on opposite side of the plunger hole to guide the second guide rails, and a second internal threaded part provided on an inner periphery of the body cap to engage with the first external threaded part.

14. The vacuum assisted auto-lancing device according to claim 12, wherein an end of the fourth chamber is closed by the plunger cap which is made of a flexible material, and a strip for testing blood glucose is placed in the fourth chamber which is closed by the plunger cap.

* * * * *